United States Patent [19]

Wallace et al.

[11] Patent Number: 4,897,244

[45] Date of Patent: Jan. 30, 1990

[54] APPARATUS AND METHODS FOR ANALYZING FLUIDS

[75] Inventors: Patrick B. Wallace, Saginaw; Larry W. Moore, Plano, both of Tex.

[73] Assignee: Abbott Laboratories, North Chicago, Ill.

[21] Appl. No.: 872,778

[22] Filed: Jun. 10, 1986

Related U.S. Application Data

[63] Continuation of Ser. No. 620,147, Jun. 13, 1984, abandoned.

[51] Int. Cl.$^4$ .................. B01L 3/02; G01N 35/06
[52] U.S. Cl. .................. 422/100; 73/864.24; 324/663; 422/63
[58] Field of Search .............. 422/63, 65, 67, 100, 422/119; 436/55; 141/83, 198; 73/863.32, 863.01, 864.24, 864.31, 304 C; 340/620; 324/61 R, 450, 446

[56] References Cited

U.S. PATENT DOCUMENTS

| | | | |
|---|---|---|---|
| 2,910,940 | 11/1959 | Colman et al. | 324/61 R |
| 3,119,266 | 1/1964 | Atkinson | 324/61 R |
| 3,635,094 | 1/1972 | Oberli | 73/864.24 X |
| 3,900,289 | 8/1975 | Liston . | |
| 4,066,412 | 1/1978 | Johnson et al. . | |
| 4,198,483 | 4/1980 | Sogi et al. | 422/100 |
| 4,326,851 | 4/1982 | Bello et al. | 422/100 |

FOREIGN PATENT DOCUMENTS 1071656 6/1967 United Kingdom ............ 324/61 R

OTHER PUBLICATIONS

*Elector,* vol. 4, No. 7–8, 1978, pp. 7–24,
*Elector,* Jul./Aug. 1980, pp. 7–22.

*Primary Examiner*—Michael S. Marcus
*Attorney, Agent, or Firm*—John W. Cornell

[57] ABSTRACT

Apparatus and methods for analyzing fluid such as blood serum. A probe used for transferring some of the fluid to a testing station causes a change in circuit capacitance when the probe contacts the fluid. This change in capacitance causes production of a control signal which effects cessation of the descent of the probe into the fluid.

1 Claim, 1 Drawing Sheet

APPARATUS AND METHODS FOR ANALYZING FLUIDS

This is a continuation of application Ser. No. 620,147 filed June 13, 1984, now abandoned.

BACKGROUND OF THE INVENTION

This invention relates to apparatus and methods used in analyzing constituent components in a fluid such as blood serum. Such apparatus and methods typically involve the application of a reagent to a sample of blood serum in a transparent laboratory vessel known as a cuvette. The reagent conventionally binds to a predetermined constituent component of the blood serum samples, thereby isolating that component for analysis by whatever means may be employed.

The blood serum sample as well as the different reagents that may be used for analysis purposes are initially placed in a suitable container. Probes are then ordinarily used to aspirate small quantities of the reagent and the blood serum sample respectively, and deposit them in the cuvette for analysis in a well-known manner. The probes are conventionally manipulated by mechanical arms such as disclosed in U.S. Pat. No. 4,326,851—Bellows, which are, in turn, under the control of microprocessor electronics. Though this technique has been successful, it is not without certain drawbacks and deficiencies which render such apparatus and methods prone to error on some occasions. More particularly, the probes used for transferring reagent and blood serum sample fluids are subject to cross-contamination and other problems which may adversely affect the results of the analysis.

For example, different reagents are, of course, used to isolate different constituent components of the blood serum sample to be analyzed. When the probe used to deposit one reagent in the cuvette is subsequently used to transfer a different reagent, residue from the first reagent often mixes with the subsequent reagent thereby contaminating the latter. Similarly, when the probe used to transfer one sample of blood serum is subsequently used to transfer a different blood serum sample, the latter sample may become contaminated with residue from the former. In either situation, the cross-contamination may result in an erroneous analysis of the sample of blood serum then being tested.

It is, therefore, a primary object of this invention to provide improvements in apparatus and methods useful in the analysis of fluid samples such as blood serum. These improvements are particularly useful in sensing the fluid level in such apparatus, permitting smaller sample volumes to be employed. It is another object of this invention to provide improved apparatus and methods for analyzing such fluids wherein the likelihood of cross-contamination is minimized, and the accuracy of the analysis is enhanced. Other objects of the invention will become apparent upon reading the detailed description of the preferred embodiment of the invention summarized below.

SUMMARY OF THE INVENTION

The foregoing objects of the invention, along with numerous features and advantages, are achieved in an apparatus for analyzing a fluid of the type utilizing a probe for transferring some of the fluid from a container to a testing station for analysis. The apparatus includes conductive means associated with the probe and impedance means, including the probe, adapted to undergo a threshold change when the conductive means contacts a fluid in the container. Circuit means are coupled to the impedance means for producing a control signal in response to the threshold change in impedance. Mechanical means, coupled to the circuit means, establish the position of the probe in the container upon receipt of the control signal, whereby the depth of the probe in the fluid can be minimized, thereby reducing the amount of residue fluid that adheres to the probe when the probe is subsequently used to transfer a different fluid.

Another aspect of the invention involves a method for controlling a probe, used in a fluid analyzing apparatus, for transferring some of the fluid from a container to a testing station in the apparatus. The method comprises the steps of supporting the container on a conductive surface of the apparatus, establishing a first capacitance between the surface and conductive means associated with the probe, causing the movement of the probe into the container so that the conductive means contacts the fluid in the container, establishing a second capacitance between the conductive surface and the fluid as a result of such movement of the probe, and stopping the movement of the probe after the second capacitance has been established, whereby the depth of the probe in the fluid in minimized.

BRIEF DESCRIPTION OF THE DRAWINGS

An exemplary embodiment of the invention summarized above is shown in the accompanying drawings where.

DETAILED DESCRIPTION OF AN EXEMPLARY EMBODIMENT OF THE INVENTION

Figure 1:
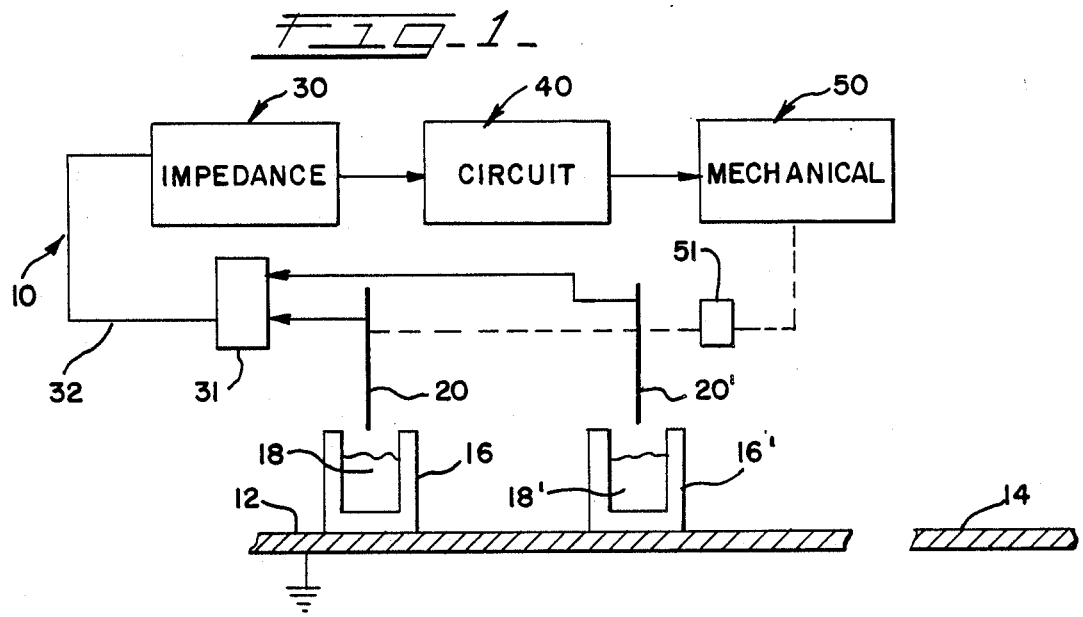
FIG. 1 is a combination schematic and block diagram of a portion of an apparatus for analyzing a fluid in accordance with the invention.

Referring now to FIG. 1 there is shown a schematic representation of a portion of an apparatus 10 for analyzing the constituent components of a fluid such as blood serum. Apparatus 10 includes an electrically conductive chassis 12 coupled to a reference potential referred to hereinafter as ground. Chassis 12 is adapted to support a container 16 which holds an ionized fluid 18.

Chassis 12 may also support a second container 16' holding a second ionized fluid 18'. Since, as explained above, apparatus 10 is utilized for analyzing the constituent components of blood serum, the fluid 18 in container 16 represents a sample of the blood serum to be analyzed. Moreover, since conventional blood serum analysis utilizes various reagents adapted to react with a blood serum sample to isolate a particular constituent component thereof, fluid 18' in container 16' is representative of one of the various reagents useful in this analysis. In this exemplary embodiment containers 16 and 16' are electrically nonconductive, and are preferably formed of styrene or high density polyethylene.

Apparatus 10 further includes a probe 20 adapted to be inserted in the fluid 18 held in container 16. In this exemplary embodiment probe 20 is formed of metal, preferably 300 series stainless steel. Probe 20 is typically used to aspirate a sample of fluid 18 (blood serum) and transport that sample by mechanical means 50 to a testing station 14 in apparatus 10 in a well-known manner.

Similarly, apparatus 10 preferably includes a second probe 20' adapted to be inserted in the fluid 18' held in container 16'. In this exemplary embodiment probe 20' is formed from an electrically conductive polymer, preferably conductive polypropylene plastic. As with probe 20, probe 20' is used to aspirate a sample of fluid 18' (reagent) and transport that sample by mechanical means 50 to the testing station 14 of apparatus 10. (The dotted lines from mechanical means 50 to probes 20, 20' are schematic representations of the mechanical connection therebetween.) After samples of blood serum and reagent are transported to testing station 14, they are deposited in a cuvette (not shown) where analysis proceeds in a manner well-known in the art.

Either one of probes 20, 20' may be alternatively coupled to mechanical means 50 by conventional mechanical probe selection means 51 associated with mechanical means 50. Mechanical means 50 may comprise a simple mechanical arm, a sophisticated robotic system, or any other mechanism for alternatively inserting probes 20, 20' into respective container 18, 18', and then transporting the probes to the testing station 14. Whatever form mechanical means 50 may take, it is preferably operated under the control of circuit means 40. Circuit means 40 are, in turn, effected by associated impedance means 30.

Impedance means 30 are coupled via a conductor 32 to probe coupling means 31. Coupling means 31 may conventionally include a receptable for receiving a jack from either probe 20 or probe 20'. Thus, either probe 20 or probe 20' can be included as part of the circuit impedance. Probe 20, or alternatively probe 20', is adapted to cause a circuit parameter to change in the circuit. In this preferred embodiment, a threshold change in impedance occurs after either probe 20 is inserted in fluid 18, or probe 20' is inserted in fluid 18'. This threshold change in impedance causes circuit means 40 to provide a control signal which controls certain aspects of the operation of mechanical means 50.

Figure 2:
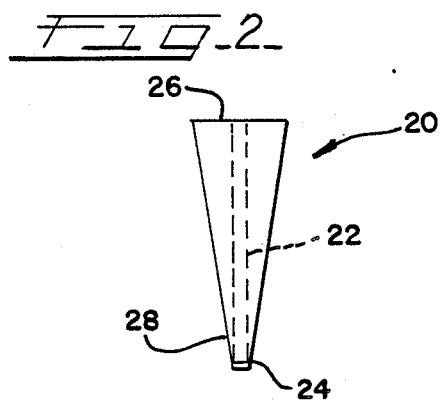
FIG. 2 is a schematic illustration of one of the probes which may be used with the apparatus of FIG. 1.

Referring now to FIG. 2, there is shown a schematic representation of a probe, such as probe 20', used in connection with apparatus 10. Probe 20' preferably has a tapered shape approximating the configuration of an inverted cone. More particularly, probe 20' is approximately 3" long, narrowing from a diameter of about 0.4" at the top to about 0.05" at the bottom. In this preferred embodiment, the probes are used for aspirating fluids, and therefore an axial opening 22 extends down the center of probe 20' from the proximal end 26 to the distal tip 24. Opening 22 is coupled to suction means (not shown) for aspirating a small quantity of fluid such as reagent and depositing that quantity into the cuvette at testing station 14. As explained above, probe 20' is preferably formed of conductive plastic, and is thus characterized by conductive means represented by reference numeral 28. Though this specific construction is preferred, the invention need not be limited to aspirating probes or a particular conductive material, the scope of the invention being defined by the appended claims.

Probe 20 is similar to the configuration of probe 20' but is preferably formed of a metal material. As such probe 20 is also characterized by conductive means. For reasons that will become more apparent hereinafter, conductive means 28 associated with probe 20, and the conductive means associated with probe 20' preferably extends substantially all the way to the distal tip of each probe.

The conductive means associated with each probe establish a probe capacitance with the grounded chassis 12 of apparatus 10 prior to the insertion of the probe into its associated container and resulting contact with the fluid held therein. In this exemplary embodiment, the probe capacitance of probe 20—prior to such contact with fluid 18—is approximately 14 pf. The probe capacitance of probe 20' under the same circumstances is also about 14 pf. On the other hand, when the conductive means 28 of probe 20 contacts fluid 18 in container 16, the probe capacitance increases to about 16 pf. This occurs because, when the conductive means 28 contacts the ionized fluid 18, this fluid effectively becomes an enlarged capacitive "plate", thereby increasing the probe capacitance. For the same reasons, the probe capacitance associated with probe 20' increases to about 25 pf when the associated conductive means contact fluid 18'. The probe capacitance (and interconnected impedances) associated with probes 20, 20' thus undergoes a threshold change when their respective conductive means contacts the ionized fluids in their corresponding containers.

The above capacitance values include an oscilloscope probe capacitance of about 13 pf.

Figure 3:
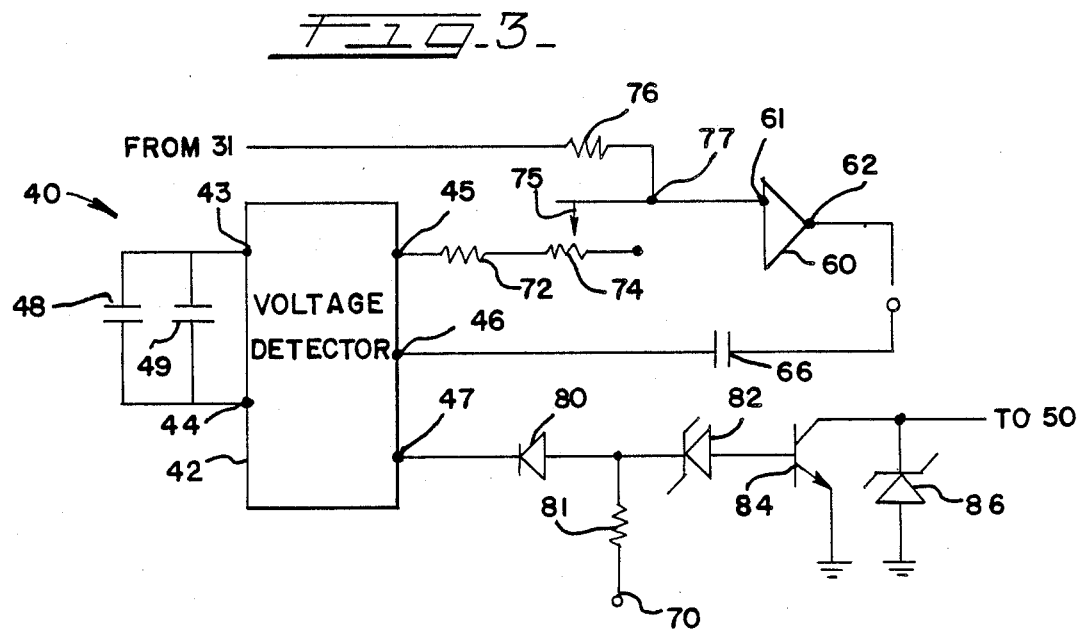
FIG. 3 is a circuit diagram representing a portion of the apparatus shown in FIG. 1.

As explained in connection with the description of FIG. 1, probe 20, or alternatively probe 20', form part of the impedance means 30 when one probe or the other is coupled via means 31 to conductor 32. This impedance is then applied to circuit means 40. The operation of circuit means 40 can be better understood by referring to FIG. 3.

Circuit means 40 include a device 42 which serves as an oscillator/voltage detector. In this exemplary embodiment device 42 is an integrated circuit LM 1830 having a plurality of terminals, including a first group of terminals 43–44, and a second group of terminals 45–47.

A variable capacitor 48, preferably adjustable between 10–120 pf, and a fixed capacitor 49 of about 50 pf are connected in parallel and coupled to terminals 43, 44 of device 42. Capacitor 48 is adjusted so that an output signal of approximately 3.4 volts peak-to-peak at 50 K Hz is produced by device 42 at terminal 45. Terminal 45 of device 42 is coupled through a fixed resistor 72 and a variable resistor 74. In this embodiment fixed resistor 72 and variable resistor 74 are approximately 1M and 2M, respectively.

Variable resistor 74 has a wiper arm 75 preferably coupled, via a node 77 and a fixed 1.2K resistor 76 to coupling means 31. When a jack (not shown), electrically connected via a conductor to probe 20, is engaged in coupling means 31, probe 20 forms part of the impedance means represented by block 30 of FIG. 1. Alternatively, if a jack (not shown), electrically connected via a conductor to probe 20' is engaged in the coupling means 31 probe 20' forms part of the impedance means 30.

Assuming probe 20 is coupled to coupling means 31, the probe capacitance (established between conductive means 28 and the grounded chassis 12 of apparatus 10) in combination with the resistance of fixed resistor 76, forms an impedance which is in shunted relationship with the resistance resulting from the action of wiper arm 75 of variable resistor 74. This impedance reduces the amplitude of the output signal generated at terminal 45 of device 42. The reduced amplitude signal is then applied to an input 61 of an operational amplifier 60.

Operational amplifier 60 is conventional, and serves to increase the gain of the signal applied at input 61. This signal is passed via a 0.01 mf capacitor 66 to terminal 46 of device 42.

If the signal applied to terminal 46 of device 42 is of sufficient amplitude, it will cause the voltage level at terminal 47 to change from "high" to ground. This, in turn, establishes a current path from a power supply 70 (+24 volts) through a 2.2K resistor 81 and a light emitting diode 80, to terminal 47. This current illuminates diode 80 in accordance with wellknown principles. Thus, diode 80 is illuminated when neither probe 20 nor probe 20' are in contact with the fluid in containers 16 and 16', respectively. Of course, if the voltage at terminal 46 is of insufficient amplitude to change the output at terminal 47 from "high" to ground, a situation which occurs when the conductive means associated with probe 20 is in contact with the fluid in container 16 (or, alternatively, when the conductive means associated with probe 20' is in contact with the fluid in container 16'), a current path is not established via diode 80, and the diode will not illuminate.

When the voltage at terminal 47 remains "high", the voltage from power supply 70 is applied via a Zener diode 82 to the base of a grounded emitter transistor 84, protected from spurious signals by a Zener diode 86. This voltage causes transistor 84 to conduct, thereby grounding the collector which was previously at a relatively high state. The transition from a high state to ground at the collector of transistor 84 constitutes, in this exemplary embodiment, a control signal which is applied to mechanical means 50.

Mechanical means 50 preferably responds to this control signal by stopping the descent of the probe, thereby establishing the position of the probe in the container. Since the control signal is generated almost immediately after the conductive means associated with the probe contacts the fluid in the container, and since the conductive means are located at the distal tip of the probe, the depth of the probe into the fluid is desirably minimized. This reduces the amount of residue fluid that will adhere to the probe, which reduces the amount of cross-contamination occurring when the probe is subsequently put into a different fluid.

The preferred operation of apparatus 10 can now be explained. Initially a container of ionized fluid such as container 16 is supported on a conductive surface of apparatus 10, such as the grounded chassis 12. A first probe capacitance is established between the grounded chassis 12 and conductive means 28 associated with probe 20. Mechanical means 50 cause the movement of probe 20 into container 16 so that the conductive means 28 at the distal tip 24 of probe 20 contacts the ionized fluid 18 in container 16. When this occurs, a second capacitance, greater than the first capacitance, is established. This change in the impedance, causes the output signal generated at terminal 62 of device 60 to be significantly reduced. This reduced output signal results in a relatively high voltage appearing at terminal 47 of device 42 which, in turn, blocks the current path through diode 80. As a result, the light emitted by diode 80 is extinguished.

The presence of a relatively high voltage at terminal 47 of device 42 causes the application of sufficient voltage to the base of transistor 84 to turn that transistor on. When transistor 84 turns on, a transistion from a high state to a grounded state occurs at its collector, resulting in a control signal which is applied to mechanical means 50. Upon receipt of the control signal, mechanical means 50 automatically stops the descent of probe 20, thereby minimizing the depth which probe 20 is immersed in fluid 18.

Fluid 18 is then aspirated from container 16 and transferred to testing station 14 for analysis in a well-known manner. Of course, as soon as conductive means 28 are taken out of contact with fluid 18, the probe capacitance decreases causing ground to appear at terminal 47 of device 42. This, of course, causes diode 80 to illuminate, signaling that probe 20 is not in contact with fluid 18. This also reduces the voltage heretofore applied to the base of transistor 84, thereby removing the control signal previously generated at the collector. The absence of this control signal will permit mechanical means 50 (under the control of its associated electronics) to again lower probe 20 into container 16 until conductive means 28 contacts fluid 18.

As mentioned above, the apparatus and methods of this invention minimize cross-contamination of fluids and therefore contribute to more accurate, reliable results on analysis. Moreover, the subject design permits a minimum fluid sample volume of about 10 microliters, reduces many of the problems heretofore associated with fluid evaporation, and effects substantial economies in equipment and operational expenses.

What has been described is an improved method and apparatus useful in the analysis of fluids such as blood serum. Though the exemplary embodiment disclosed herein is preferred, numerous variations and modifications which do not part from the true scope of the invention will be apparent to those skilled in the art. All such variations and modifications are intended to be covered by the appended claims.

We claim:

1. Apparatus for sensing the top level of a fluid in a container, comprising the combination of:
   an open container made of nonconductive material for holding an ionized fluid whose top level in the container is to be sensed,
   a chassis having a flat conductive surface disposed below the container and supporting the container thereon,
   probe means having one end adapted to be moved into and out of the open top of the container under the control of mechanical means, said probe including means for transferring the fluid from said container to a testing station for analysis,
   electrical conductor means at said one end of the probe,
   the cross-sectional area of said one end of the probe being small relative to the area of said flat conductive surface on which the container is supported and small relative to said container,
   a source of a.c. signals,
   means for coupling said conductor means at said one end of the probe to receive a.c. signals from said source of a.c. signals,
   an electrical ground associated with said source of a.c. signals,
   means for connecting said conductive surface of the chassis to said electrical ground,
   said conductor means on the probe and said chassis defining a capacitor means and the magnitude of the capacitance changing from one value to a larger value when the probe end is first brought into contact with ionized fluid in the container,
   impedance means including said capacitor means adapted to undergo a threshold signal change when the conductor means on the probe contacts fluid in the container, and
   circuit means coupled to said impedance means for producing a control signal to said threshold signal change.

* * * * *